United States Patent
Suh et al.

(10) Patent No.: US 10,343,958 B2
(45) Date of Patent: Jul. 9, 2019

(54) CATALYST FOR COATING SURFACE OF POROUS MATERIAL AND METHOD OF TREATING SURFACE OF POROUS MATERIAL

(71) Applicant: LG CHEM, LTD., Seoul (KR)

(72) Inventors: Myung Ji Suh, Daejeon (KR); Jun Han Kang, Daejeon (KR); Dong Hyun Ko, Daejeon (KR); Seong Min Kim, Daejeon (KR); Hyun Seok Nam, Daejeon (KR); Joo Hyuck Lee, Daejeon (KR); Kyong Yong Cha, Daejeon (KR); Dae Heung Choi, Daejeon (KR); Sang Jin Han, Daejeon (KR); Jun Kyu Han, Daejeon (KR); Sun Hwan Hwang, Daejeon (KR); Ye Seul Hwang, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days.

(21) Appl. No.: 15/561,316

(22) PCT Filed: Mar. 30, 2017

(86) PCT No.: PCT/KR2017/003464
§ 371 (c)(1),
(2) Date: Sep. 25, 2017

(87) PCT Pub. No.: WO2017/183829
PCT Pub. Date: Oct. 26, 2017

(65) Prior Publication Data
US 2018/0186711 A1    Jul. 5, 2018

(30) Foreign Application Priority Data

Apr. 18, 2016 (KR) .......... 10-2016-0046693

(51) Int. Cl.
*C07C 5/48* (2006.01)
*B01J 35/04* (2006.01)
(Continued)

(52) U.S. Cl.
CPC ............... *C07C 5/48* (2013.01); *B01J 23/74* (2013.01); *B01J 23/78* (2013.01); *B01J 23/80* (2013.01);
(Continued)

(58) Field of Classification Search
CPC ...................................................... C07C 5/48
See application file for complete search history.

(56) References Cited

U.S. PATENT DOCUMENTS 3,420,912 A * 1/1969 Karkalits, Jr. ............ C07C 5/42
585/444
3,849,511 A * 11/1974 Manning ................ B01J 23/862
585/433
(Continued)

FOREIGN PATENT DOCUMENTS

KR    10-2012-0009687 A    2/2012
KR       10-1340620 B1    12/2013
WO       2012-030891 A1    3/2012

*Primary Examiner* — Douglas B Call
(74) *Attorney, Agent, or Firm* — Dentons US LLP (57) ABSTRACT

The present invention relates to a catalyst for coating a surface of a porous material and a method of treating the surface of the porous material. More particularly, when the catalyst for coating a surface of a porous material and the method of treating the surface of the porous material of the present invention are used for butadiene synthesis reaction under high gas space velocity and high pressure conditions, heat generation may be easily controlled and differential pressure may be effectively alleviated, thereby providing improved reactant conversion rate and product selectivity.

9 Claims, 1 Drawing Sheet

(51) Int. Cl.
  *B01J 23/80*   (2006.01)
  *B01J 37/02*   (2006.01)
  *B01J 37/08*   (2006.01)
  *B01J 37/03*   (2006.01)
  *B01J 35/02*   (2006.01)
  *B01J 37/00*   (2006.01)
  *B01J 23/74*   (2006.01)
  *B01J 23/78*   (2006.01)
  *B01J 23/84*   (2006.01)
  *C07C 7/20*   (2006.01)
  *C07C 11/08*   (2006.01)

(52) U.S. Cl.
  CPC ............ *B01J 23/84* (2013.01); *B01J 35/023* (2013.01); *B01J 35/04* (2013.01); *B01J 37/00* (2013.01); *B01J 37/009* (2013.01); *B01J 37/02* (2013.01); *B01J 37/0215* (2013.01); *B01J 37/0236* (2013.01); *B01J 37/031* (2013.01); *B01J 37/08* (2013.01); *C07C 7/20* (2013.01); *C07C 11/08* (2013.01)

(56) References Cited

U.S. PATENT DOCUMENTS

| | | |
|---|---|---|
| 3,849,545 A | 11/1974 | Miklas |
| 4,150,064 A | 4/1979 | Miklas |
| 4,916,105 A | 4/1990 | Rieck et al. |
| 2004/0199034 A1* | 10/2004 | Walsdorff ............... C07C 5/327 585/310 |
| 2004/0225165 A1* | 11/2004 | Allison ................... C07C 29/06 568/910.5 |
| 2013/0158325 A1* | 6/2013 | Kwon ................... B01J 23/8892 585/625 |
| 2014/0141965 A1 | 5/2014 | Xiong et al. |

* cited by examiner

CATALYST FOR COATING SURFACE OF POROUS MATERIAL AND METHOD OF TREATING SURFACE OF POROUS MATERIAL

CROSS-REFERENCE TO RELATED APPLICATION

This application is a National Stage Entry of International Application No. PCT/KR2017/003464 filed on Mar. 30, 2017, and claims the benefit of Korean Application No. 10-2016-0046693, filed on Apr. 18, 2016, all of which are hereby incorporated by reference in their entirety for all purposes as if fully set forth herein.

TECHNICAL FIELD

The present invention relates to a catalyst for coating a surface of a porous material and a method of treating the surface of the porous material. More particularly, the present invention relates to a catalyst for coating a surface of a porous material and a method of treating the surface of the porous material, wherein the surface of the porous material is coated with the catalyst, whereby heat generation is easily controlled under high gas space velocity and high-pressure butadiene synthesis reaction conditions and differential pressure is effectively alleviated, resulting in a high conversion rate of a reactant and product selectivity.

BACKGROUND ART 1,3-Butadiene is used as an intermediate in producing petrochemical products and demand therefor and value thereof are gradually increasing throughout the world. Such 1,3-butadiene is produced by naphtha cracking, direct dehydrogenation of butene, oxidative dehydrogenation of butene, or the like. However, since a naphtha cracking process has high energy consumption due to high reaction temperature and a problem that other basic oils other than 1,3-butadiene are produced in a surplus because the process is not highly selective for 1,3-butadiene. In addition, direct dehydrogenation of n-butene is not only thermodynamically disadvantageous, but also requires high-temperature and low-pressure conditions for the production of 1,3-butadiene with high yield due to being an endothermic reaction. Accordingly, direct dehydrogenation of n-butene is not suitable for industrial production of 1,3-butadiene.

Meanwhile, oxidative dehydrogenation of butene is a reaction in which butene and oxygen react with each other in the presence of a metal oxide catalyst to produce 1,3-butadiene and water. Since stable water is produced by the reaction, the reaction is thermodynamically advantageous. In addition, oxidative dehydrogenation of butene is exothermic, unlike direct dehydrogenation of butene, 1,3-butadiene may be obtained in a high yield even at a low reaction temperature as compared to direct dehydrogenation. Further, since oxidative dehydrogenation of butene does not require additional heat supply, it may become an effective standalone production process to meet demand for 1,3-butadiene.

However, in synthesis of 1,3-butadiene through oxidative dehydrogenation, heat is excessively generated due to oxidation reaction of producing COx which is a side reaction, an increase in an internal temperature of a catalyst bed due to heat generation may accelerate oxidation reaction of producing COx and the speed of side reaction of producing heavies. In this case, it is difficult to control to heat with filled-type pellets, and differential pressure increases.

Therefore, there is a need for development of a filled-type metal oxide catalyst that is used for oxidative dehydrogenation of butene and is capable of maintaining a high conversion rate by controlling heat generation and alleviating differential pressure under conditions of high gas space velocity (GHSV) and high pressure.

RELATED ART DOCUMENT (Patent Document 1) KR 2012-0009687 A

DISCLOSURE

Technical Problem

Therefore, the present invention has been made in view of the above problems, and it is one object of the present invention to provide a filled-type catalyst for coating a surface of a porous material, the filled-type catalyst being capable of maintaining a high conversion rate by controlling heat generation and alleviating differential pressure under conditions of high gas space velocity (GHSV) and high pressure, and a method of treating the surface of the porous material.

It is yet another object of the present invention to provide a method of preparing butadiene using the catalyst for coating a surface of a porous material.

The above and other objects can be accomplished by the present disclosure described below.

Technical Solution

In accordance with one aspect of the present invention, provided is a catalyst for coating a surface of a porous material including a porous metal oxide material with a hole structure including 200 pores per square inch (ppi) or less; and a metal oxide loaded on the porous material surface, wherein the metal oxide has a composition represented by Formula 1 below and a powder form having a particle size of 0.85 mm or less:

[Formula 1]

wherein A is one or more selected from the group consisting of divalent cation metals.

In accordance with another aspect of the present invention, provided is a method of coating a surface of a porous material with a water-based composition for coating a surface of a porous material, the method including a step of preparing a porous metal oxide material; a step of immersing the porous metal oxide material in a water-based coating composition; and a step of removing the porous metal oxide material from the water-based coating composition and aerating the same, followed by drying the same.

In accordance with yet another aspect of the present invention, there is a method of preparing butadiene using the catalyst for coating a surface of a porous material.

Advantageous Effects

As apparent from the fore-going, when a catalyst for coating a surface of a porous material and a method of treating the surface of the porous material of the present invention are used for butadiene synthesis under high gas space velocity and high pressure conditions, heat generation may be easily controlled and differential pressure may be effectively alleviated, thereby providing improved reactant conversion rate and product selectivity. In addition, the porous material may be simply, rapidly surface-treated under aqueous conditions, and damage to the porous material may be prevented.

BEST MODE

Hereinafter, the present invention is described in detail.

As a catalyst for coating a surface of a porous material according to the present invention, a water-based composition for coating a porous material surface may be used. The water-based composition for a porous material surface is useful for a porous material surface, particularly a porous metal oxide material surface.

The water-based composition for coating a porous material surface of the present invention is based on water and includes a ferritic metal oxide and a stabilizer. Selectively, the water-based composition may further include other additives. Since the water-based composition for coating a porous material surface of the present invention does not include an oxidant, influence of the water-based composition on chemical state of the porous material surface is small.

The ferritic metal oxide included in the coating composition of the present invention forms a blackened layer on a surface of a coated porous material, whereby the ferritic metal oxide forms more catalytic active sites on a wide surface area of the porous material. Accordingly, reaction performance may be improved during synthesis of butadiene, and accumulation of heat generation and differential pressure may be alleviated due to a porous or hollow structure.

In the present invention, the ferritic metal oxide refers to a metal oxide having a composition represented by Formula 1 below, and may be a single metal oxide or a composite oxide including a plurality of metal atoms:

$$AFe_2O_4 \quad \text{[Formula 1]}$$

wherein A may be, for example, one or more selected from the group consisting of divalent cation metals. As a particular example, A may be one or more selected from the group consisting of Zn, Mg, and Mn. Preferably, A is Zn.

When A is one or more metals, the ferritic metal oxide represented by Formula 1 may be represented by, for example, $(Zn, Mn)Fe_2O_4$, $(Zn, Mg)Fe_2O_4$, $(Mg, Mn)Fe_2O_4$, or $(Zn, Mg, Mn)Fe_2O_4$. In this case, the ferritic metal oxide may be understood as a mixture of ferritic metal oxides including divalent cations in parentheses. As a particular example, in the case of $(Zn, Mn)Fe_2O_4$, the ferritic metal oxide represents a mixture of metal oxides having compositions of $ZnFe_2O_4$ and $MnFe_2O_4$.

The ferritic metal oxide having the composition represented by Formula 1 may be, for example, a ferritic metal oxide having a spinel structure. The structure may be understood as a structure wherein a unit lattice of a cubic system is composed of eight divalent cations, 16 trivalent cations, and 32 oxygen ions, the oxygen ions mostly forming a face-centered cubic lattice that is filled with divalent cations (A) and trivalent cations (Fe).

The ferritic metal oxide may include, for example, 0.01 to 10 mol % of an iron oxide (a metal oxide having a structure such as $\alpha\text{-}Fe_2O_3$, $\beta\text{-}Fe_2O_3$, $\gamma\text{-}Fe_2O_3$, $Fe_3O_4$, FeO, or the like) due to Fe not binding to A.

The ferritic metal oxide may be prepared by coprecipitating, for example, a precursor material including A and Fe and may be included, in a metal oxide powder form after being dried and fired, in the water-based composition for coating.

In the composition for coating a surface of the present invention, the ferritic metal oxide may be included in a ratio of 10 to 900 parts by weight, for example in a ratio of 10 to 900 g/L, in a ratio of 15 to 500 g/L, in a ratio of 20 to 300 g/L, or in a ratio of 50 to 200 g/L. Within this range, a surface of the porous material may be sufficiently blackened.

The stabilizer included in the composition for coating a surface of the present invention causes the ferritic metal oxide to be stably maintained in the composition of the present invention. As the stabilizer included in the present invention, one or more selected from among polyvinyl pyrrolidone (PVP), 2-hydroxyethyl methacrylate (HEMA), polyacrylic acid (PAA), polystyrene sulfonate (PSS), polyethylene imine (PEI), poly-L-lysine (PLL), poly(lactic-coglycolic acid) (PLSA), polylactic acid (PLA), polyglycolic acid (PGA), dextrin, dextran, dextran derivatives, chitosan, and chitosan derivatives may be used. In the composition for coating a surface of the present invention, the stabilizer may be included in a content of 1 to 100 parts by weight, for example, in a content of 1 to 100 g/L, in a content of 1 to 50 g/L, or in a content of 10 to 50 g/L. Within this range, particles of the ferritic metal oxide may be stabilized without being detached or peeled off from the porous material surface. For reference, the stabilizer is a material required during a surface coating process, and is not included in the composition of the catalyst for coating.

The composition for coating a porous material surface of the present invention may include, other than the aforementioned ingredients, only water. That is, the composition may include the aforementioned ingredients and water. Alternatively, the composition may further include, other than the aforementioned ingredients and water, additives generally used in the art. The additives are not separately disclosed because they are well known to those of ordinary skill in the art.

Water used in the composition for coating a porous material surface of the present invention may be deionized water generally used in the art. As needed, the water may be water remaining in a coprecipitated slurry that is generated in a process of preparing a ferritic metal oxide. The content of water in the composition of the present invention may be 100 to 1000 parts by weight, for example, 100 to 1000 g/L, 200 to 950 g/L, or 250 to 900 g/L.

In the coating composition of the present invention, for example, the ferritic metal oxide and the water may be mixed in a specific ratio. A weight ratio of the ferritic metal oxide to the water may be, for example, 1:20 to 5:1, or 1:2 to 2:1. When a ratio of the ferritic metal oxide to the water is within this ratio, the thickness of a substance coated on the porous material may be controlled, whereby pores and holes of the porous material are not blocked. Accordingly, surface area increase due to coating may be accomplished.

The catalyst of the present invention is a water-based composition for a porous material surface, and includes a porous metal oxide material with a hole structure including 200 pores per square inch (ppi) or less; and a metal oxide loaded on the porous material surface. Wherein the metal oxide has a composition represented by Formula 1 below and is a powder having a particle size of 0.85 mm or less:

$$AFe_2O_4 \qquad \text{[Formula 1]}$$

wherein A is one or more selected from the group consisting of divalent cation metals.

As described above, the ferritic metal oxide is prepared by coprecipitating a precursor material including A and Fe, and may be provided in a metal oxide powder form through drying, firing, and the like.

The metal oxide powder may be pulverized, for example, to a particle size of 0.85 mm or less, 0.001 to 0.6 mm, 0.001 to 0.5 mm, or 0.001 to 0.25 mm. Within this range, separation and detachment of the ferritic metal oxide coated on the porous material surface may be prevented. In the present invention, a particle size of the metal oxide powder is included within the range.

When the catalyst includes 1 to 50 parts by weight or 1 to 30 parts by weight of the ferritic metal oxide based on 100 parts by weight of the porous metal oxide material, a surface blackened layer may be sufficiently formed.

The present invention provides a method of coating a porous material surface with the water-based composition for a porous material surface. The method may include a step of preparing a porous metal oxide material; a step of immersing the porous metal oxide material in a water-based coating composition; and a step of removing the porous metal oxide material from the water-based coating composition and aerating the same, followed by drying the same. Here, as the water-based coating composition, the composition for coating a porous material surface of the present invention may be used.

Figure 1:
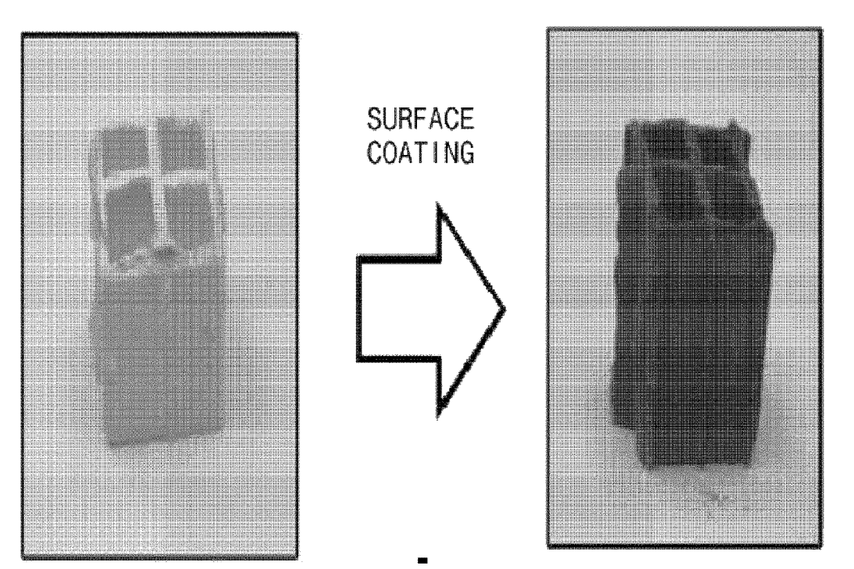
FIG. 1 illustrates a porous material surface-coated with a water-based composition as a coating catalyst. More particularly, a left drawing illustrates a ceramic monolith-type porous material made of a ceramic material having fine pores before surface coating, and a right drawing illustrates a porous material on which a blackened layer is formed after being surface-coated with the catalyst for coating a surface.

Hereinafter, the catalyst for coating a surface of a porous material of the present invention and a method of treating the surface of the porous material are described with reference to FIG. 1. FIG. 1 illustrates a porous material surface-coated with a water-based composition as a coating catalyst. More particularly, a left drawing illustrates a ceramic monolith-type porous material made of a ceramic material having fine pores before surface coating, and a right drawing illustrates a porous material on which a blackened layer is formed after being surface-coated with the catalyst for coating a surface. The surface treatment method of the present invention may be used to form a structure illustrated in a right photograph of FIG. 1. Particularly, the surface treatment method is useful for formation of a coating layer/blackened layer on an entire surface including, in addition to an outer circumferential surface of the porous material, the surfaces of fine pores (voids) formed by ceramic material particles.

Hereinafter, a method of forming a structure illustrated in FIG. 1 using the method of the present invention is described.

Step 1 of the surface treatment method of the present invention is a step of preparing a porous material. As the porous material, a porous metal oxide material used in the field of catalysis may be used.

The porous metal oxide material is a structure prepared by molding a crystalline solid to have a hole structure and easily contacts the flow of gas in an oxidative dehydrogenation reaction process. That is, since a ferritic metal oxide coated on a wide surface area of a porous material may form more catalytic active sites, accumulation of heat generation and differential pressure due to a hole structure may be alleviated. Accordingly, the porous metal oxide material is advantageously applicable to oxidative dehydrogenation.

Particularly, the porous metal oxide material may be a porous material molded with a ceramic material so that columnar passages having a predetermined diameter are arranged in parallel. The passages may be, for example, holes. Cross sections of the holes may have, for example, a circular or polygonal shape. Here, the polygonal shape may be, for example, a square or hexagonal shape. In addition, the ceramic material may form irregular micropores or voids.

The porous metal oxide material refers to a structure with holes capable of providing both heat generation control effect and differential pressure alleviation effect when used in oxidative dehydrogenation for butadiene production. For example, the porous metal oxide material may have a spherical shape, a cylindrical shape, a hexahedral shape, a rectangular shape, a monolith shape, or the like.

As needed, the porous metal oxide material may be a cut product prepared by cutting a commercially available product to a certain size. The height of the cut product may be, for example, 5 to 25 mm, 5 to 20 mm, or 5 to 10 mm in width×length×height.

The hole structure of the porous metal oxide material may be formed by, for example, 200 pores square per inch (ppi) or less, 10 to 200 ppi, 50 to 180 ppi, or 100 to 150 ppi. Within this range, the ferritic metal oxide may be sufficiently coated (or stacked) on a surface of the porous material, and holes having a proper size may be secured by the coated (or stacked) ferritic metal oxide. Such holes may be provided as sites for heat generation control and differential pressure alleviation.

In the present disclosure, to find ppi, the number of pores on a one-inch by one-inch line using a WI-QA-14 (in accordance with ASTM) may be accurately counted and an average value thereof may be calculated.

The porous metal oxide material may have, for example, a columnar hollow structure wherein the diameters of holes are 1 to 20 mm, 1 to 10 mm, or 2 to 5 mm. For reference, with regard to the porous metal oxide material, the diameters of micropores (voids) formed by ceramic material particles may be, for example, 1000 µm or less, 0.01 to 800 µm, or 0.01 to 600 µm, and surface areas thereof may be, for example, 1 to 100 m$^2$/L, 1 to 50 m$^2$/L, or 1 to 10 m$^2$/L.

In the present disclosure, a surface area and an average pore size may be respectively calculated according to the BET equation and the BJH method.

The porous metal oxide material may be, for example, one or more selected from the group consisting of metal oxides, metal carbides, metal nitrides, and hydrated aluminum silicate. In addition, various ceramic monoliths or and the like used as a supporter of a ferritic metal oxide may be used. As a particular example, one or more selected from the group consisting of kaolinite, dickite, nacrite, halloysite, cordierite, diatomite, aluminum nitride (AlN), silicon nitride ($Si_3N_4$), silicon carbide (SiC), zirconium carbide (ZrC), tungsten carbide (WC), alumina ($Al_2O_3$), mullite, and zirconia ($ZrO_2$) may be used. The aluminum silicate may be kaolin.

A porous metal oxide material made of cordierite is preferred because it is inactive to oxidative dehydrogenation or has very low catalytic activity and thus is effective as a non-competitive physical support of ferritic metal oxide.

The surface treatment method of the present invention includes a subsequent step of immersing the porous metal oxide material using a water-based coating composition. Here, the water-based coating composition may include 10 to 900 parts by weight of the aforementioned ferritic metal oxide, 1 to 100 parts by weight of a stabilizer, and 100 to 1000 parts by weight of water. For example, the water-based coating composition may include 10 to 900 g/L of the ferritic metal oxide, 1 to 100 g/L of a stabilizer, and 100 to 1000 g/L of water.

As a particular example, the water-based coating composition may be a coprecipitated slurry of a metal precursor (a precursor of a metal oxide) prepared by coprecipitating a metal precursor including A and Fe with a precipitant or a ferritic metal oxide slurry prepared by adding water and a stabilizer to a ferritic metal oxide powder formed by filtering, drying, and firing the coprecipitated metal precursor slurry.

The coprecipitated metal precursor slurry may be obtained, for example, through the following steps:

First, a secondary cation metal (A) precursor and a Fe(III) precursor are dissolved in distilled water, thereby preparing an aqueous precursor solution.

Subsequently, the aqueous precursor solution is added dropwise to a coprecipitation tank containing a basic aqueous solution. Here, the aqueous precursor solution may be added dropwise along with a basic aqueous solution the same or different from the aqueous basic in the solution coprecipitation tank to constantly maintain the pH of a coprecipitation solution.

Subsequently, the coprecipitation solution is filtered, thereby preparing a coprecipitated slurry including the precursor of the metal oxide (metal precursor) or a catalyst slurry including a ferritic metal oxide having a composition represented by Formula 1 below:

[Formula 1]

wherein A is one or more selected from the group consisting of divalent cation metals.

For example, the basic aqueous solution contained in the coprecipitation tank and the basic aqueous solution added dropwise to the coprecipitation tank may be aqueous solutions having the same concentration and pH, aqueous solutions having different concentrations or pH, or different basic aqueous solutions. As a particular example, each of the basic aqueous solutions may be an aqueous sodium hydroxide solution or an aqueous ammonia solution.

The pH of each of the basic aqueous solutions may be, for example, 8 to 11, 8 to 10, or 9 to 9.5. Within this range, iron oxide generation in a catalyst is minimized, whereby selectivity and yield depending upon oxidative dehydrogenation are superior.

The basic aqueous solution added dropwise is provided to constantly maintain the pH of the coprecipitation solution changed due to the aqueous precursor solution added dropwise to the coprecipitation tank. Within a range within which the pH of the coprecipitation solution is constantly maintained, the basic aqueous solution might not be added or may be added dropwise along with the aqueous precursor solution, or only the basic aqueous solution may be independently added dropwise.

For example, the aqueous precursor solution and the basic aqueous solution from separate outlets may be simultaneously added dropwise. In this case, pH change in the coprecipitation solution, which is changed due to the aqueous precursor solution added dropwise to the coprecipitation tank, may be constantly maintained by controlling a dripping amount of the basic aqueous solution.

A method of preparing the ferritic metal oxide may include, for example, a step of stirring the coprecipitation solution to which the aqueous precursor solution has been completely added dropwise. In this case, coprecipitation of the precursor in the coprecipitation solution may be sufficiently performed. The stirring may be performed, for example, for 0.5 to 24 hours, 0.5 to 16 hours, or 0.5 to 3 hours.

The catalyst composition may be prepared, for example, by diluting a metal oxide having the composition represented by Formula 1 with water. Here, the metal oxide having the composition represented by Formula 1 may be prepared, for example, by vacuum-filtering the coprecipitated slurry to obtain a precipitate and drying the obtained precipitate. The dried precipitate may be fired, for example, by elevating temperature up to 400 to 1000° C., 500 to 800° C., or 600 to 700° C. at a temperature elevation rate of 0.5 to 10° C./min, 0.5 to 5° C./min, or 0.3 to 3° C./min and then maintaining the elevated temperature for 2 to 48 hours, 2 to 24 hours, or 4 to 16 hours. In this case, the metal precursor is crystallized, thereby forming a crystal structure of a ferritic metal oxide having the composition represented by Formula 1.

A weight ratio of the ferritic metal oxide (catalyst) to water may be, for example, 10:1 to 1:10, 5:1 to 1:5, or 2:1 to 1:2. In this case, holes of the porous metal oxide material are not blocked. Accordingly, a surface stabilizer may be used as an additive for increasing adhesiveness of the porous material.

The stabilizer is required only in a coating process and is not included in the composition of a final coating catalyst. The stabilizer may be added, for example, in an amount of 10% by weight or less, 0.01 to 8% by weight, or 0.01 to 5% by weight based on a total weight of the catalyst slurry (or water-based coating composition).

The ferritic metal oxide having the composition represented by Formula 1 may be obtained, for example, in a metal oxide powder form through the firing step. The metal oxide powder may be pulverized, for example, to a particle size of 0.85 mm or less, or 0.01 to 0.5 mm, 0.01 to 0.25 mm, or 0.05 to 0.1 mm. In this case, detachment and exfoliation of the metal oxide coated on the porous metal oxide material may be prevented. A particle size of the pulverized metal oxide powder is included in the particle size range.

Subsequently, a step of removing the porous metal oxide material from the water-based coating composition and aerating the same, followed by drying the same, is performed. Aeration means that the porous metal oxide material is aerated by the coprecipitated slurry or the catalyst slurry such that holes of the coated porous metal oxide material are not blocked. Gas used for aeration may be, for example, air, nitrogen gas, helium gas, or argon gas. The pressure and temperature of the gas are not specifically limited so long as the coating effect is maintained.

The coated porous metal oxide material may be dried, for example, at 50 to 250° C., 80 to 200° C., or 100 to 150° C. for 0.5 to 48 hours, 0.5 to 24 hours, or 0.5 to 20 hours. Within this range, water is completely removed.

The immersion, aeration and drying steps may be repeated twice to four times, or twice to three times. In this case, the ferritic metal oxide is sufficiently provided on the porous metal oxide material.

The method of treating the surface of the porous material may include, for example, a step of firing the coated porous metal oxide material. The step of firing the coated porous metal oxide material may be performed, for example, by elevating temperature up to 250 to 1000° C., 300 to 800° C., or 350 to 700° C. at a temperature elevation rate of 0.5 to 10° C./min, 0.5 to 5° C./min, or 0.3 to 3° C./min and then maintaining the elevated temperature for 1 to 48 hours, to 24 hours, or 2 to 16 hours. In this case, crystallization and binding of the porous metal oxide material and the coated ferritic metal oxide proceed, thereby preventing detachment thereof from the porous metal oxide material.

A catalyst for coprecipitation may be prepared, for example, by dissolving the divalent cation metal (A) precursor and the Fe(III) precursor in distilled water to prepare an aqueous precursor solution and adding the aqueous precursor solution to a coprecipitation tank containing the aqueous basic solution dropwise. When the aqueous precursor solution is added to the coprecipitation tank, a basic aqueous solution the same as or different from the aqueous basic solution may be simultaneously added dropwise. Accordingly, the catalyst may be obtained while constantly maintaining the pH of the coprecipitation solution in a pH range of 8 to 11.

A step of performing oxidative dehydrogenation reaction of a reactant using the catalyst for coating of the present invention is included in the method of the present invention, and may be used to prepare butadiene. Oxidative dehydrogenation reaction refers to a reaction wherein olefin is reacted with oxygen in the presence of a metal oxide to generate conjugated diene and water. As a particular example, the oxidative dehydrogenation reaction may be a reaction wherein butane is reacted with oxygen to generate 1,3-butadiene and water.

In the oxidative dehydrogenation reaction, a butene conversion rate may be, for example, 80% or more, 80 to 99.9%, or 83.3 to 99.9%.

In the oxidative dehydrogenation reaction, the selectivity of 1,3-butadiene may be, for example, 80% or more, 80 to 99.9%, or 85 to 97%.

A reactor used in the oxidative dehydrogenation reaction is not specifically limited so long as it has been used in oxidative dehydrogenation reaction. For example, the reactor may be a reactor wherein reaction temperature of an installed catalyst layer is maintained constant, and oxidative dehydrogenation reaction of a reactant is performed while the reactant continuously passes through the catalyst layer. As a particular example, the reactor may be a tubular reactor, a tank-type reactor, a fluidized-bed reactor, or a fixed-bed reactor. Here, the fixed-bed reactor may be, for example, a multi-tubular reactor or a plate-type reactor.

A reactant subjected to the oxidative dehydrogenation reaction may include, for example, one or more selected from the group consisting of butane, isobutane, 1-butene, trans-2-butene, and cis-2-butene and oxygen. The reactant may further include nitrogen gas and steam.

The amount of the oxygen may be, for example, 0.5 to 5 moles, 0.5 to 3 moles, or 0.6 to 1.5 moles based 1 mole of the reactant, the amount of the nitrogen gas may be, for example, 0 to 30 moles, 2 to 25 moles, or 2 to 15 moles based 1 mole of the reactant, and the amount of the steam may be, for example, 2 to 50 moles, 3 to 30 moles, or 4 to 25 moles based 1 mole of the reactant. Within this range, superior catalytic activity is exhibited.

During the oxidative dehydrogenation reaction, a gas space velocity (GHSV) may be, for example, 20 to 1000 $h^{-1}$, 50 to 750 $h^{-1}$, or 80 to 650 $h^{-1}$ based on the reactant.

During the oxidative dehydrogenation reaction, reaction temperature (T) may be, for example, 300 to 500° C., 320 to 400° C., or 320 to 380° C. Within this range, conversion into butadiene is activated and side reaction to Cox is minimized, whereby superior butene conversion rate and butadiene selectivity are exhibited.

During the oxidative dehydrogenation reaction, reaction pressure may be, for example, 0 psig to 10 bar, 0 psig to 5 bar, or 0 psig to 3 bar.

With regard to 0 psig of the present disclosure, most pressure gauges, pressure transmitters, or other pressure gauges are designed to indicate gauge pressure, and thus, when exposed to atmospheric pressure, indicate zero pressure, i.e., 0 psig.

In the oxidative dehydrogenation reaction, the selectivity of butadiene to butene may be 83% or more, or 83 to 88%, for example, under conditions such as 340° C., gas space velocity (GHSV) of 450 to 750 $h^{-1}$, and a butene partial pressure of 0 to 12 psig.

In the oxidative dehydrogenation reaction, the selectivity of Cox to butene may be 15% or less, or 9 to 15%, for example, under conditions such as 340° C., a gas space velocity (GHSV) of 450 to 750 $h^{-1}$, and a butene partial pressure of 0 to 12 psig.

In the oxidative dehydrogenation reaction, a conversion rate of reacted butene to supplied butene may be 85% or more, or 85 to 96%, for example, under conditions such as 340° C., a gas space velocity (GHSV) of 450 to 750 $h^{-1}$, and a butene partial pressure of 0 to 12 psig.

In the oxidative dehydrogenation reaction, the highest temperature (hot spot) of the catalyst layer may be 418 to 501° C., for example, under conditions such as 340° C., a gas space velocity (GHSV) of 450 to 750 $h^{-1}$, and a butene partial pressure of 0 to 12 psig.

Now, the present invention will be described in more detail with reference to the following preferred examples. However, these examples are provided for illustrative purposes only. Those skilled in the art will appreciate that various modifications, additions and substitutions are possible, without departing from the scope and spirit of the invention. Therefore, it is obvious that the modifications, additions and substitutions are within the scope of the present invention.

EXAMPLE

<Preparation of Porous Metal Oxide Material>

A porous metal oxide material used in an experiment was prepared as follows:

Each of a monolith with a columnar hole structure made of cordierite and having 100 pores per square inch (ppi), a monolith with a columnar hole structure made of cordierite and having 50 ppi, and a monolith with a columnar hole structure made of cordierite and having 300 ppi was cut into a size of 8 mm×8 mm×10 mm in width×length×height and washed with distilled water, followed by drying at 120° C. for 16 hours. As a result, three kinds of porous metal oxide materials were prepared (see the left photograph of FIG. 1).

Preparation Example 1

In step 1, the porous metal oxide material with a columnar hole structure having 100 ppi was selected from among the three porous materials.

In step 2, a coprecipitated slurry was prepared as follows:

12 g of a zinc precursor ($ZnNO_3$) and 48 g of an iron precursor ($FeCl_3$) (mole ratio of Zn:Fe=1:2) were dissolved in room-temperature distilled water, thereby preparing an aqueous metal precursor solution. Subsequently, an aqueous ammonia solution having pH of 9 at room temperature was prepared in a coprecipitation tank having a capacity of 3 to 10 L, an aqueous metal precursor solution and 25 wt % of an aqueous ammonia solution were simultaneously added thereto dropwise by means of individual peristaltic pumps while stirring the aqueous ammonia solution at room temperature, and coprecipitation was performed while maintaining the pH of a coprecipitation solution in the coprecipitation tank at 9 to 9.5. As a result, a coprecipitated slurry was prepared.

The coprecipitated slurry was subjected to vacuum filtration, thereby obtaining a dark brown precipitate. The precipitate was dried in a 90° C. oven for 16 hours, and a dried dark maroon solid was fired, thereby obtaining a metal oxide catalyst powder.

Here, after a firing process in air was performed at a rate of 1 L/min in a firing furnace, the firing furnace was continuously charged until the temperature of the firing furnace reached room temperature. During firing, a firing temperature was elevated up to 650° C. at a temperature elevation rate of 1° C./min and the elevated temperature was maintained for six hours.

An obtained metal oxide was subjected to XRD analysis. As a result, the presence of 99 mol % of $ZnFe_2O_4$ and 1 mol % of iron oxide ($\alpha$-$Fe_2O_3$) was confirmed. The metal oxide was pulverized and sieved such that all particles thereof had a size of 0.25 mm or less, thereby being prepared into a powder form.

In step 3, 500 g/L of the ferritic metal oxide powder, 500 g/L of water, and 10 g/L of dextrin were added thereto, thereby preparing a water-based composition for coating. Subsequently, a porous metal oxide material having a hole distribution of 100 ppi was immersed in the water-based composition for coating such that all surfaces of the porous material contacted the water-based composition.

In step 4, the porous metal oxide material was removed from the water-based composition and then aerated, followed by drying at 120° C. for one hour. Subsequently, the dried porous metal oxide material was immersed in a water-based composition for coating again and aerated, followed by drying. These immersing, aerating, and drying processes were repeated three times, thereby preparing a catalyst wherein a porous metal oxide material was coated with a ferritic metal oxide.

Preparation Example 2

A catalyst for coating was prepared in the same manner as in Preparation Example 1, except that the temperature of a catalyst for coating prepared in step 4 was elevated up to 650° C. at a temperature elevation rate of 1° C./min under an air atmosphere, the elevated temperature was maintained for six hours, and firing was additionally performed. For reference, adhesiveness of a ferritic metal oxide to a porous metal oxide material of the catalyst for coating of Preparation Example 2 was improved compared to that of the catalyst for coating of Preparation Example 1.

Preparation Example 3

10 g/L of dextrin was added to 1000 g/L of the coprecipitated slurry obtained in step 2 of Preparation Example 1, thereby preparing a water-based coating composition (the vacuum filtration, drying, and firing processes of step 2 were omitted).

In addition, referring to step 4 of Preparation Example 1, the porous metal oxide material was removed from the water-based composition and then aerated, followed by drying at 90° C. for three hours. The dried porous metal oxide material was re-immersed in the water-based coating composition and aerated, followed by drying. These immersion, aeration, and drying processes were repeated three times. Subsequently, firing was performed at 650° C. for six hours under an air atmosphere, thereby preparing a catalyst for coating.

Preparation Example 4

A catalyst for coating was prepared in the same manner as in Preparation Example 1, except that, in step 1, a porous metal oxide material with a columnar hole structure having 50 ppi was used instead of the porous metal oxide material with a columnar hole structure having 100 ppi.

Preparation Example 5

Step 1 of Preparation Example 1 was omitted (the porous metal oxide material was not used), and a coprecipitated slurry obtained in step 2 was subjected to vacuum filtration and fired at 650° C. for six hours at a temperature elevation rate of 1° C./min, thereby preparing a granular ferrite metal oxide (steps 3 and 4 of Preparation Example 1 were omitted).

Preparation Example 6

A granular ferrite metal oxide was prepared in the same manner as in Preparation Example 5, except that, in step 2, a zinc precursor and an iron metal precursor were used in a mole ratio of 1.5:2.

The prepared metal oxide was subjected to XRD analysis, and a result thereof was as follows: $ZnFe_2O_4$: 96 mol %, ZnO: 4 mol %.

Preparation Example 7

A granular ferrite metal oxide was prepared in the same manner as in Preparation Example 5, except that, in step 2, a zinc precursor and an iron metal precursor were used in a mole ratio of 1:2.5.

The prepared metal oxide was subjected to XRD analysis, and a result thereof was as follows: $ZnFe_2O_4$: 80 mol %, iron oxide ($\alpha$-$Fe_2O_3$): 20 mol %.

Preparation Example 8

A catalyst for coating was prepared in the same manner as in Preparation Example 1, except that, in step 1, a porous metal oxide material with a columnar hole structure having 300 ppi was used instead of the porous metal oxide material with a columnar hole structure having 100 ppi.

Preparation Example 9

A catalyst for coating was prepared in the same manner as in Preparation Example 1, except that, upon pulverization of step 2, a metal oxide was sieved such that all particles thereof had a size of 1 mm or less, thereby being prepared into a powder form.

Test Example

Using the catalyst for coating prepared in each of Preparation Examples 1 to 9, butadiene was prepared according to the following examples and comparative examples. Results are summarized in Table 2 below.

Examples 1 to 6 and Comparative Examples 1 to 7

Butadiene Preparation

A mixture of 1-butene, trans-2-butene, and cis-2-butene and oxygen were used as reactants, and nitrogen gas and steam were additionally introduced thereinto. As a reactor, a metallic tubular fixed-bed reactor was used. The reactor was filled with 10 cc of a catalyst, and a ratio of the reactants (mole ratio) and gas hourly space velocity (GHSV) were set based on the butene mixture as summarized in Table 1 below. Water was injected into a reactor, and vaporized in a steam form at 250° C. by means of a vaporizer. The steam was mixed with the butene mixture and oxygen as reactants, and introduced into the reactor. After reaction, a product was analyzed by gas chromatography (GC). Based on the gas chromatography analysis result, a conversion rate (X_butene) of the butene mixture, selectivity to butadiene or COx (S_1,3-butadiene, S_CO$_x$), and yield were calculated according to Equations 1 to 3 below. Results are summarized in Table 2 below.

Conversion rate (%)=(Number of moles of reacted butene/number of moles of supplied butene)× 100 [Equation 1]

Selectivity (%)=(Number of moles of generated 1,3-butadiene or COx/number of moles of reacted butene)×100 [Equation 2]

Yield (%)=(Number of moles of generated 1,3-butadiene/number of moles of supplied butene)×100 [Equation 3]

TABLE 1

| Classification | Used catalyst | Reaction temperature (° C.) | Reaction pressure (psig) | Oxygen relative to butene | Steam relative to butene | Nitrogen gas relative to butene | Gas space velocity (h$^{-1}$) |
| --- | --- | --- | --- | --- | --- | --- | --- |
| Example 1 | Preparation Example 1 | 340 | 0 | 1 | 5 | 4 | 750 |
| Example 2 | Preparation Example 1 | 340 | 0 | 1 | 5 | 4 | 450 |
| Example 3 | Preparation Example 1 | 340 | 12 | 1 | 5 | 4 | 450 |
| Example 4 | Preparation Example 2 | 340 | 0 | 1 | 5 | 4 | 450 |
| Example 5 | Preparation Example 3 | 340 | 0 | 1 | 5 | 4 | 450 |
| Example 6 | Preparation Example 4 | 340 | 0 | 1 | 5 | 4 | 450 |
| Comparative Example 1 | Preparation Example 5 | 340 | 0 | 1 | 5 | 4 | 750 |
| Comparative Example 2 | Preparation Example 5 | 340 | 0 | 1 | 5 | 4 | 450 |
| Comparative Example 3 | Preparation Example 5 | 340 | 12 | 1 | 5 | 4 | 450 |
| Comparative Example 4 | Preparation Example 6 | 340 | 0 | 1 | 5 | 4 | 450 |
| Comparative Example 5 | Preparation Example 7 | 340 | 0 | 1 | 5 | 4 | 450 |
| Comparative Example 6 | Preparation Example 8 | 340 | 0 | 1 | 5 | 4 | 450 |
| Comparative Example 7 | Preparation Example 9 | 340 | 0 | 1 | 5 | 4 | 450 |

TABLE 2

| Classification | Conversion rate (%) | S_BD (%) | Yield (%) | S_CO$_x$ (%) | Hot spot (° C.) |
| --- | --- | --- | --- | --- | --- |
| Example 1 | 85.4 | 83.3 | 71.1 | 14.9 | 501 |
| Example 2 | 95.0 | 84.3 | 80.1 | 13.7 | 432 |
| Example 3 | 90.4 | 81.5 | 73.7 | 15.7 | 439 |
| Example 4 | 94.8 | 87.5 | 83.0 | 10.3 | 426 |
| Example 5 | 94.4 | 88.0 | 83.0 | 9.3 | 422 |
| Example 6 | 95.9 | 87.8 | 84.1 | 9.1 | 418 |
| Comparative Example 1 | 80.1 | 76.3 | 61.1 | 16.7 | 520 |
| Comparative Example 2 | 84.3 | 83.8 | 70.6 | 14.4 | 432 |
| Comparative Example 3 | 78.6 | 80.6 | 63.4 | 16.8 | 441 |
| Comparative Example 4 | 6.7 | 24.2 | 1.6 | 45.1 | — |
| Comparative Example 5 | 84.3 | 81.7 | 68.9 | 15.1 | 444 |
| Comparative Example 6 | 84.3 | 82.6 | 77.9 | 14.1 | 447 |
| Comparative Example 7 | 86.2 | 83.1 | 71.6 | 14.8 | 450 |

S_BD, S_CO$_x$, and S_BP: Respectively indicate 1,3-butadiene (BD) selectivity and CO$_x$ selectivity.
Hot spot (° C.): The highest temperature of a catalyst layer measured by means of a thermocouple.

As shown in Tables 1 and 2, when the catalysts for coating of Preparation Examples 1 to 8 were respectively used under the same butadiene synthesis conditions, Example 2, 4, 5, and 6 exhibited superior butene conversion rate, butadiene selectivity, and yield were exhibited, compared to Comparative Examples 2, 4, 5, and 6.

Meanwhile, in the cases of Comparative Examples 1 and 2, butadiene yield was decreased and COx selectivity and hot spot increased, as gas space velocity increased. On the other hand, when the catalysts for coating of Examples 1 and 2 according to the present invention were used, decrease in butadiene yield was reduced and increase in COx selectivity and hot spot was alleviated, compared to Comparative Examples 1 and 2.

In addition, in the cases of Comparative Examples 2 and 3, a butadiene yield was decreased and COx selectivity and hot spot increased as pressure increased. On the other hand, when the catalysts for coating of Examples 2 and 3 according to the present invention were used, decrease in butadiene yield was reduced and increase in COx selectivity and hot spot was alleviated, compared to Comparative Examples 2 and 3.

Further, after completing preparation of the catalyst for coating of Comparative Example 7, a hole clogging phenomenon or an exfoliation phenomenon were observed. Accordingly, it can be confirmed that the catalyst of Comparative Example 7 is poor, compared to Example 2 having the same conversion rate, selectivity, yield, and hot spot and the same preparation and reaction conditions except for the size of pulverized particles.

Additional Experimental Example 1

Experimental Examples of Various Porous Metal Oxide Materials

Using various porous materials summarized in Table 3 below, experimentation was carried out under the same reaction conditions as in Example 1. Referring to Table 3, Blank indicates a result of an experiment performed using an empty reactor without use of a catalyst and a porous material, and by-product yield (%) indicates a value of conversion rate×(100-butadiene selectivity)/100. This by-product yield (%) corresponds to a generation ratio of other by-products except for COx and hydrocarbon-based butadiene.

TABLE 3

| Classification | Conversion rate (%) | Selectivity (%) | By-product yield (%) |
|---|---|---|---|
| Blank | 0.8 | 19.7 | 0.6 |
| Cordierite | 3.0 | 50.6 | 1.5 |
| SiC | 11.6 | 31.6 | 7.9 |
| Silicon nitride | 30.7 | 59.3 | 12.5 |
| Silica | 5.2 | 14.1 | 4.5 |
| Alpha-alumina | 6.8 | 33.2 | 4.5 |
| Bentonite | 4.9 | 38.1 | 3.0 |
| Kaolin | 11.8 | 41.4 | 6.9 |
| Boehmite | 21.7 | 10.6 | 19.4 |

As shown Table 3, it can be confirmed that, when the porous cordierite material is used, the yield of undesired by-products is lowest, whereby the porous cordierite material is effective as a non-competitive physical support of a ferritic metal oxide that is inert to oxidative dehydrogenation reaction or has very low catalytic activity.

In addition, it can be confirmed that bentonite, silica, alpha-alumina, kaolin, and SiC are applicable in this order.

Additional Experimental Example 2

Additional Preparation Example 1

A catalyst for coating was prepared in the same manner as in Preparation Example 1, except that 50 g/L of a ferritic metal oxide powder, 500 g/L of water, and 50 g/L of dextrin were added in step 3, and a water-based composition for coating was prepared.

Additional Preparation Example 2

A catalyst for coating was prepared in the same manner as in Preparation Example 1, except that 500 g/L of a ferritic metal oxide powder and 100 g/L of water were added (dextrin was not added) in step 3, and a water-based composition for coating was prepared.

Additional Preparation Example 3

A catalyst for coating was prepared in the same manner as in Preparation Example 1, except that 30 g/L of a ferritic metal oxide powder, 1000 g/L of water, and 100 g/L of dextrin were added in step 3, and a water-based composition for coating was prepared.

Additional Preparation Example 4

A catalyst for coating was prepared in the same manner as in Preparation Example 1, except that 600 g/L of a ferritic metal oxide powder and 100 g/L of water were added (dextrin was not added) in step 3, and a water-based composition for coating was prepared.

Additional Preparation Example 5

A catalyst for coating was prepared in the same manner as in Preparation Example 1, except that 500 g/L of a ferritic metal oxide powder, 100 g/L of water, and 150 g/L of dextrin were added in step 3, and a water-based composition for coating was prepared.

The catalyst for coating of each of Additional Preparation Examples 1 to 5 was used in a butadiene synthesis experiment under the same reaction conditions as in Example 2. Results are summarized in Table 4 below.

TABLE 4

| Classification | Conversion rate (%) | S_BD (%) | Yield (%) | S_COx (%) | Hot spot (° C.) |
|---|---|---|---|---|---|
| Additional Preparation Example 1 | 93.1 | 86.9 | 80.9 | 10.1 | 431 |
| Additional Preparation Example 2 | 94.2 | 85.2 | 80.3 | 9.7 | 432 |
| Additional Preparation Example 3 | 71.8 | 85.1 | 61.1 | 14.2 | 442 |
| Additional Preparation Example 4 | 84.9 | 82.9 | 70.4 | 13.8 | 441 |
| Additional Preparation Example 5 | 87.1 | 84.9 | 73.9 | 15.5 | 445 |

S_BD, S_COx, and S_BP: Respectively indicate 1,3-butadiene (BD) selectivity and COx selectivity.
Hot spot (° C.): The highest temperature of a catalyst layer measured by means of a thermocouple.

As shown in Table 4, it can be confirmed that, when the catalyst for coating of each of Additional Preparation Examples 1 and 2 is used in the butadiene synthesis reaction, catalytic activity similar to that of Preparation Example 1 is exhibited. Accordingly, it can be confirmed that Additional Preparation Examples 1 and 2 are suitable as preparation examples to provide superior butene conversion rate, butadiene selectivity, and yield.

On the other hand, after completing preparation of the catalysts for coating of Additional Preparation Examples 4 and 5, a hole clogging phenomenon or an exfoliation phenomenon was observed. In addition, in the case of the catalyst for coating of Additional Preparation Example 3, a surface of the porous material was partially exposed. That is, it was observed with the naked eye that blackening due to coating with the ferritic metal oxide was not sufficiently performed. Further, when the catalyst of Additional Preparation Example 3 was used in the butadiene synthesis reaction, a butene conversion rate was decreased.

From these results, the present inventors confirmed that the catalyst for coating of the present invention was effective in alleviating differential pressure and heat generation under high gas space velocity and high-pressure reaction.

The invention claimed is:

1. A method of treating a surface of a porous material, the method comprising:
    a step of preparing an aqueous precursor solution by dissolving a secondary cation metal (A) precursor and a Fe(III) precursor in distilled water;
    a step of adding the aqueous precursor solution to a coprecipitation tank containing a first aqueous basic solution dropwise, wherein the aqueous precursor solution is added dropwise along with a second aqueous basic solution, wherein the first aqueous basic solution is the same as or different from the first aqueous basic solution to constantly maintain pH of a coprecipitation solution;
    a step of preparing a coprecipitated slurry comprising a precursor of a metal oxide or a catalyst slurry comprising a ferritic metal oxide having a composition represented by Formula 1 below by stirring the coprecipation solution:

$$AFe_2O_4;$$ [Formula 1]

a step of filtering the coprecipated slurry or the catalyst slurry to separate the precursor of the metal oxide and the ferritic metal oxide, respectively;
    a step of preparing a water-based coating composition by either mixing the precursor of the metal oxide separated from the coprecipitated slurry with a stabilizer or adding water and a stabilizer to the ferritic metal oxide separated from the catalyst slurry;
    a step of selecting a porous metal oxide material having a hole structure comprising 200 ppi (pores per square inch) or less;
    a step of immersing the porous metal oxide material in the water-based coating composition; and
    a step of removing the porous metal oxide material from the water-based coating composition and aerating the porous metal oxide material, followed by drying the porous metal oxide material;
    wherein A is one or more selected from the group consisting of Zn, Mg and Mn, and
    wherein the water-based coating composition comprises 50 to 900 parts by weight of a ferritic metal oxide, 10 to 100 parts by weight of a stabilizer, and 100 to 1000 parts by weight of water.

2. The method according to claim 1, wherein the stabilizer is one or more selected from among polyvinyl pyrrolidone (PVP), 2-hydroxyethyl methacrylate (HEMA), polyacrylic acid (PAA), polystryrene sulfonate (PSS), polyehylene imine (PEI), poly-L-lysine (PLL), poly(lactic-coglycolic acid) (PLSA), polylactic acid (PLA), polyglycolic acid (PGA), dextrin, dextran, dextran derivatives, chitosan, and chitosan derivatives.

3. The method according to claim 1, wherein a weight ratio of the ferritic metal oxide to the water is 1:10 to 10:1.

4. The method according to claim 1, wherein pH of the coprecipitation solution is maintained within a range of 8 to 11.

5. The method according to claim 1, wherein the ferritic metal oxide separated from the coprecipitated ferritic metal oxide slurry is subjected to vacuum filtration to obtain a precipitate, wherein the obtained precipitate is dried and fired and then pulverized to a particle size of 0.85 mm or less.

6. The method according to claim 5, wherein the firing of the dried precipitate is performed by heating to an elevated temperature of 400 to 1000° C. at temperature elevation rate of 0.5 to 10° C./min and then maintaining the elevated temperature for 2 to 48 hours.

7. The method according to claim 1, wherein the drying of the porous metal oxide material is performed at 50 to 250° C. for 0.5 to 48 hours.

8. The method according to claim 1, wherein the immersing, aerating, and drying are repeated up to four times.

9. The method according to claim 1, comprising a step of firing the porous metal oxide material by heating to an elevated temperature of 250 to 1000° C. at a temperature elevation rate of 0.5 to 10° C./min and then maintaining the elevated temperature for 1 to 48 hours.

* * * * *